United States Patent
Wong et al.

(10) Patent No.: US 10,510,028 B2
(45) Date of Patent: Dec. 17, 2019

(54) METHOD AND APPARATUS FOR UTILIZING TASK VALUE UNITS FOR IMAGING INTERPRETATION AND OTHER TASKS

(71) Applicant: Change Healthcare Holdings, LLC, Nashville, TN (US)

(72) Inventors: Eldon Wong, Vancouver (CA); Albert Lai, Burnaby (CA); Alexander Kouzin, Richmond (CA); Faisal Muslih, Vancouver (CA); Gavin Wong, Vancouver (CA); Laurie Bergeron, Montreal (CA); Raymond Chau, Burnaby (CA)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 290 days.

(21) Appl. No.: 14/553,217

(22) Filed: Nov. 25, 2014

(65) Prior Publication Data
US 2016/0148146 A1 May 26, 2016

(51) Int. Cl.
*G16H 40/20* (2018.01)
*G06Q 10/06* (2012.01)
*G06F 19/00* (2018.01)

(52) U.S. Cl.
CPC ... *G06Q 10/063114* (2013.01); *G06F 19/321* (2013.01)

(58) Field of Classification Search
CPC ........... G06Q 10/063112; G06Q 10/10; G06Q 10/1093; G06Q 10/063116; G06F 9/4887; G16H 40/20
See application file for complete search history.

(56) References Cited

U.S. PATENT DOCUMENTS 6,456,239 B1 * 9/2002 Werb .................. G01S 5/02
                                                        235/385
2004/0049506 A1 * 3/2004 Ghouri ................ G06F 19/326
(Continued)

OTHER PUBLICATIONS

Workflow Management Coalition—Wikipedia, the free encyclopedia [online] [retrieved Jan. 11, 2016]. Retrieved from the Internet: <http://en.wikipedia.org/wiki/Workflow_Management_Coalition>. (dated Dec. 19, 2015) 4 pages.
(Continued)

*Primary Examiner* — Jonathan Durant
*Assistant Examiner* — Chad A Newton
(74) *Attorney, Agent, or Firm* — Alston & Bird LLP

(57) ABSTRACT

A method, apparatus and computer program product are provided in order to utilize task value units for imaging interpretation and other tasks, such as in the assignment of imaging interpretation and other tasks to a plurality of users. In the context of a method, the method associates, for each of a plurality of different types of imaging interpretation tasks and for each of a plurality of other tasks, a first task value unit therewith. The method also associates, for at least some of the plurality of different types of imaging interpretation or other tasks, a second task value unit, different than the first task value unit, therewith. Further, the method assigns imaging interpretation and other tasks to a plurality of users based at least partially upon the first and second task value units associated with the respective imaging interpretation tasks and the other tasks.

17 Claims, 7 Drawing Sheets

(56) References Cited

U.S. PATENT DOCUMENTS

| | | | | |
|---|---|---|---|---|
| 2004/0260576 | A1* | 12/2004 | Wang | G06F 19/325 |
| | | | | 705/2 |
| 2005/0246189 | A1* | 11/2005 | Monitzer | G06Q 10/06 |
| | | | | 705/400 |
| 2006/0064321 | A1* | 3/2006 | Sasano | G06F 19/321 |
| | | | | 705/2 |
| 2007/0282476 | A1* | 12/2007 | Song | G06F 19/327 |
| | | | | 700/100 |
| 2015/0052058 | A1* | 2/2015 | McCown | G06Q 50/22 |
| | | | | 705/51 |
| 2016/0098173 | A1* | 4/2016 | Slawinski | G06F 16/904 |
| | | | | 715/739 |

OTHER PUBLICATIONS

Workflow Management Coalition Glossary and Terminology [online] [retrieved Jan. 11, 2016]. Retrieved from the Internet: <http://www.aiai.ed.ac.uk/project/wfmc/ARCHIVE/DOCS/glossary/glossary.html>. (dated Jun. 1996) 38 pages.

Benjamin, M. et al., *From Shared Data to Sharing Workflow: Merging PACS and Teleradiology*, European Journal of Radiology 73(1) (2010) 3-9.

Seigel, E. et al., *Evolving Technology: Distributed Diagnosis* [online] [retrieved Nov. 20, 2014]. Retrieved from the Internet: <http://www.appliedradiology.com/articles/evolving-technology-distributed-diagnosis>. (dated 2008) 11 pages.

* cited by examiner

| Task Type | Task | First TVU | Second TVU |
|---|---|---|---|
| Interpretation (Study) | CXR (2 view) | 2 | 7 |
| | CT Head wo contrast | 4 | 12 |
| | CT A w/wo contrast | 5 | 15 |
| | MR Head w/wo contrast | 5 | 15 |
| | MR Knee wo contrast | 3 | 10 |
| | Xray Hand | 1 | 5 |
| | US Abd Complete | 2 | 7 |
| | NM HIDA | 6 | 15 |
| Quality | Peer Review | 2 | 0 |
| | Critical Result Follow-up | 3 | 0 |
| | Resident Review | 2 | 0 |
| | Tech QA | 1 | 0 |
| Communication | Consult | 2 | 5 |
| | Referring Clinician Inquiry | 5 | 0 |
| | IM Message | 1 | 0 |
| Other | 1 Hour Conference | 10 | 10 |
| | Rounds | 12 | 10 |
| | Biopsy | 15 | 15 |

Figure 4

| Rotation | Tasks |
|---|---|
| Mammography (8:00 am – 5:00 pm) | Diagnostic Mammo |
| | Screening Mammo |
| | General Radiology |
| MSK (8:00 am – 5:00 pm) | ER/Inpatient MSK |
| | Outpatient MSK |
| | General Radiology |
| Neurology (8:00 am – 5:00 pm) | Stroke Protocols |
| | ER/Inpatient Neurology |
| | Outpatient Neurology |
| | General Radiology |

Figure 6a

| Rotation | Oct-01 | Oct-02 | Oct-03 | Oct-04 | Oct-05 |
|---|---|---|---|---|---|
| Mammo Rotation | Dr. A<br>Dr. B | Dr. C<br>Dr. E | Dr. D<br>Dr. A | Dr. F<br>Dr. A | Dr. D<br>Dr. A |
| MSK Rotation | Dr. C<br>Dr. D | Dr. D<br>Dr. F | Dr. E<br>Dr. B | Dr. C<br>Dr. B | Dr. F<br>Dr. E |
| Neuro Rotation | Dr. E<br>Dr. F | Dr. A<br>Dr. B | Dr. C<br>Dr. F | Dr. E<br>Dr. D | Dr. B<br>Dr. C |

Figure 6b

METHOD AND APPARATUS FOR UTILIZING TASK VALUE UNITS FOR IMAGING INTERPRETATION AND OTHER TASKS

TECHNOLOGICAL FIELD

An example embodiment of the present invention relates generally to the assignment of imaging interpretation and other tasks to a plurality of users and, more particularly, to the use of task value units for the assignment of imaging interpretation and other tasks to the plurality of users.

BACKGROUND

Healthcare practitioners perform a wide variety of tasks throughout their work day. A number of the tasks are billable activities and must be assigned and tracked accordingly. However, most healthcare practitioners also perform an appreciable number of other ad hoc tasks throughout their work day. These other ad hoc tasks may be more difficult to take into account, but they may consume at least a portion and, in some instances, a substantial portion of the work day of the healthcare practitioners.

For example, a radiologist may perform a number of imaging interpretation tasks throughout the day. In performing an imaging interpretation task, a radiologist may review a medical image study and may provide a report or other feedback regarding the medical image study and the condition of the patient. In addition to performing imaging interpretation tasks, a radiologist may also be called upon to perform a wide variety of other tasks throughout their work day. For example, these other tasks may include peer reviews, technical question and answer tasks, critical result workflow tasks, consultations, teaching file management tasks, responding to inquiries from referring physicians, reviews of residents, performing rounds and other ad hoc tasks. These other tasks performed by a radiologist may consume a portion of the work day, but may be difficult to take into account or otherwise track in the same manner that the imaging interpretation tasks performed by the radiologist are tracked.

With respect to imaging interpretation tasks, medical image studies may be assigned to radiologist such that the radiologist then interprets the medical image study and provides a report or other feedback. The assigned imaging interpretation task is added to the work list of the radiologist, providing a listing of tasks to be performed by the radiologist. However, the imaging interpretation tasks may be assigned to the radiologist without knowledge or without otherwise taking into account the schedule of the radiologist or the availability of the radiologist, thereby potentially subjecting the imaging interpretation task to delay in an instance in which the radiologist is unavailable or otherwise not working for a period of time. In an effort to avoid dependence upon an individual radiologist, imaging interpretation tasks may be assigned to a work list associated with a group of radiologists. Radiologists within the group may then select imaging interpretation tasks from the work list for review. In some instances, however, a radiologist of such a group that works from a common work list may select the simpler imaging interpretation tasks and may avoid the more complex imaging interpretation tasks, thereby delaying the more complex imaging interpretation tasks and fostering an environment that is not conducive of teamwork.

In terms of work lists for individual radiologists, the work lists for some radiologists may become much larger than the work lists for other radiologists. As such, some imaging interpretation tasks will be performed much more quickly than others, merely as a result of the radiologist to which the imaging interpretation task was assigned. As such, manual efforts to balance the workload between a plurality of radiologists have sometimes been implemented. In order to facilitate workload balancing, a value unit for each imaging interpretation task may be assigned in recognition that some imaging interpretation tasks are more complex than other imaging interpretation tasks. Thus, manual efforts to balance the workload between a plurality of radiologists, not merely based upon the number of imaging interpretation tasks assigned to the radiologists, but also based on the value units of the imaging interpretation tasks assigned to the radiologists such that each radiologist has a relatively even mix of more simple and more complex imaging interpretation tasks. As a result of the manual nature of these workload balancing efforts, workload balancing has not been particularly efficient, particularly with respect to taking into account the plurality of other ad hoc tasks, other than imaging interpretation tasks, that a radiologist is commonly asked to additionally perform.

BRIEF SUMMARY

A method, apparatus and computer program product are provided in accordance with an example embodiment in order to utilize task value units for imaging interpretation and other tasks, such as in the assignment of imaging interpretation and other tasks to a plurality of users. By associating task value units not only with imaging interpretation tasks, but also with other tasks, the method, apparatus and computer program product of an example embodiment assigns the various tasks in a more fully informed manner by taking into account not only the other imaging interpretation tasks already assigned to a user, but also the other tasks that the user has been asked to perform. Further, a user is able to more completely account for their work day, such as by documenting not only the imaging interpretation tasks that were performed, but also the other tasks performed by the user throughout the day.

In an example embodiment, a method is provided for utilizing task value units for imaging interpretation and other tasks. The method of this example embodiment includes associating, for each of a plurality of different types of imaging interpretation tasks and for each of a plurality of other tasks, a first task value unit therewith. The method of this example embodiment also includes associating, for at least some of the plurality of different types of imaging interpretation or other tasks, a second task value unit, different than the first task value unit, therewith. A method of this example embodiment also includes assigning imaging interpretation and other tasks to a plurality of users based at least partially upon the first and second task value units associated with the respective imaging interpretation tasks and the other tasks.

The other tasks may include one or more of peer review tasks, technical question and answer tasks, critical result workflow tasks, teaching file management tasks, consult tasks or resident review tasks. A method of an example embodiment assigns imaging interpretation and other tasks to a plurality of users by defining a rotation that includes a plurality of types of medical image studies and assigning imaging interpretations to the plurality of users associated with the rotation. The method of an example embodiment associates a first task value unit with an imaging interpretation or other task by determining the first task value unit in accordance with a rule configuration and processing technique. The rule configuration and processing technique includes determining that a trigger has occurred. In response to occurrence of the trigger, the rule configuration and processing technique of this example embodiment evaluates one or more conditional expressions that depend upon one or more attributes. The rule configuration and processing technique then assigns the first task value unit based upon a task value unit associated with the conditional expression that was successfully evaluated. In an example embodiment, the method associates the first task value unit with an imaging interpretation or other task by determining the first task value unit in accordance with one of the rule configuration and processing technique or a look-up technique in an instance in which a predetermined condition is satisfied and, alternatively, determining the first task value unit in accordance with another of the rule configuration and processing technique or the look-up technique in an instance in which the predetermined condition is not satisfied. The predetermined condition of an example embodiment is dependent upon the value of an attribute. The method of an example embodiment associates a first task value unit with an imaging interpretation or other task by determining the first task value unit in accordance with a look-up technique that utilizes key value mapping based upon respective values of one or more attributes.

In another example embodiment, an apparatus is provided for utilizing task value units for imaging interpretation and other tasks. The apparatus includes task value unit association circuitry configured to associate, for each of a plurality of different types of imaging interpretation tasks and for each of a plurality of other tasks, a first task value unit therewith. The task value unit association circuitry is also configured to associate, for at least some of the plurality of different types of imaging interpretation or other tasks, a second task value unit, different than the first task value unit, therewith. The apparatus of this example embodiment also includes task assignment circuitry configured to assign imaging interpretation and other tasks to a plurality of users based at least partially upon at least one of the first and second task value units associated with the respective imaging interpretation and other tasks.

The other tasks may include one or more peer review tasks, technical question and answer tasks, critical result workflow tasks, teaching file management tasks, consult tasks or resident review tasks. The task assignment circuitry of an example embodiment is configured to assign imaging interpretation and other tasks to a plurality of users by defining a rotation that includes a plurality of types of medical image studies and assigning imaging interpretation tasks to a plurality of users associated with the rotation. In an example embodiment, the task value unit association circuitry is configured to associate a first task value unit with an imaging interpretation or other task by determining the first task value unit in accordance with a rule configuration and processing technique. In this embodiment, the task value unit association circuitry is configured to perform the rule configuration and processing technique by determining that a trigger has occurred and, in response to occurrence of the trigger, to evaluate one or more conditional expressions that depend upon one or more attributes. The task value unit association circuitry of this example embodiment is also configured to assign the first task value unit based upon a task value unit associated with the conditional expression that was successfully evaluated. The task value unit association circuitry of an example embodiment is also be configured to associate a first task value unit with an imaging interpretation or other task by determining the first task value unit in accordance with one of the rule configuration and processing technique or a look-up technique in an instance in which a predetermined condition is satisfied and, alternatively, to determine the first task value unit in accordance with another of the rule configuration and processing technique or the look-up technique in an instance in which the predetermined condition is not satisfied. The predetermined condition of an example embodiment is dependent upon the value of an attribute. The task value unit association circuitry of an example embodiment is also configured to associate a first task value unit with an imaging interpretation or other task by determining the first task value unit in accordance with a look-up technique that utilizes key value mapping based upon respective values of one or more attributes.

In a further example embodiment, a computer program product for utilizing task value units for imaging interpretation and other tasks is provided. The computer program product includes a non-transitory computer readable storage medium having program code portions stored thereon with the program code portions configured, upon execution, to associate, for each of a plurality of different types of imaging interpretation tasks and for each of a plurality of other tasks, a first task value unit therewith. The program code portions of this example embodiment are also configured, upon execution, to associate, for at least some of the plurality of different types of imaging interpretation or other tasks, a second task value unit, different than the first task value unit, therewith. The program code portions of this example embodiment are further configured, upon execution, to assign imaging interpretation and other tasks to a plurality of users based at least partially upon at least one of the first and second task value units associated with respect of imaging interpretation and other tasks.

The other tasks may include one or more of peer review tasks, technical question and answer tasks, critical result workflow tasks, teaching file management tasks, consult tasks or resident review tasks. The program code portions configured to assign imaging interpretation and other tasks to a plurality of users includes, in one example embodiment, program code portions configured to define a rotation that includes a plurality of types of medical image studies and to assign imaging interpretation tasks to a plurality of users associated with the rotation. The program code portions configured to associate a first task value unit with an imaging interpretation or other task includes, in an example embodiment, program code portions configured to determine the first task value unit in accordance with a rule configuration and processing technique. The rule configuration and processing technique of this example embodiment includes determining that a trigger has occurred and, in response to an occurrence of a trigger, evaluating one or more conditional expressions that depend upon the one or more attributes. The rule configuration and processing technique of this example embodiment also includes assigning the first task value unit based upon the task value unit associated with the conditional expression that was successfully evaluated. The program code portions configured to associate a first task value unit with an imaging interpretation or other task includes, in an example embodiment, program code portions configured to determine the first task value unit in accordance with one of the rule configuration and processing technique or a look-up technique in an instance in which a predetermined condition is satisfied and, alternatively, to determine the first task value unit in accordance with another of the rule configuration and processing technique or the look-up technique in an instance in which the predetermined condition is not satisfied. The predetermined condition of an example embodiment is dependent upon the value of an attribute.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Figure 1:
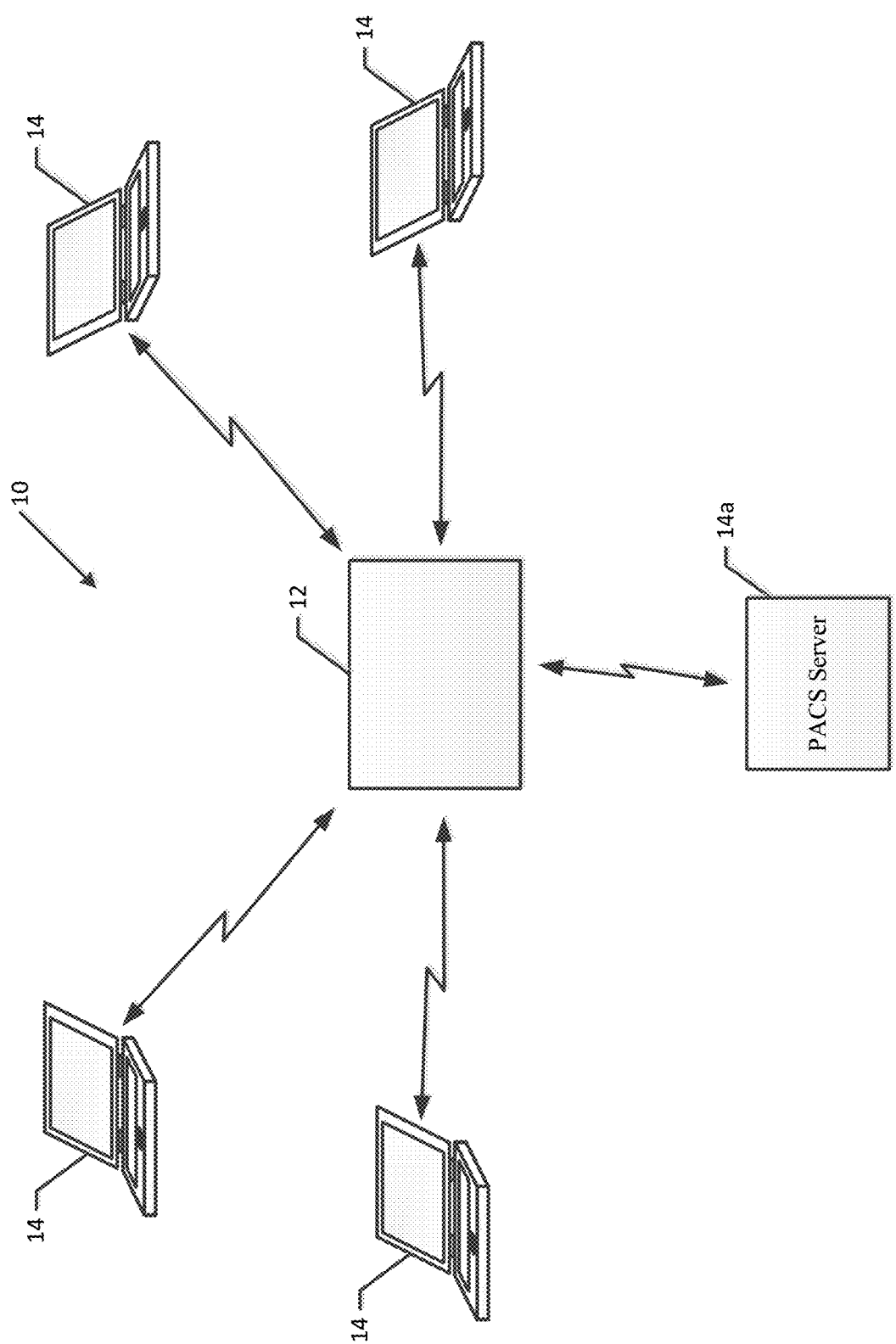
Figure 2:
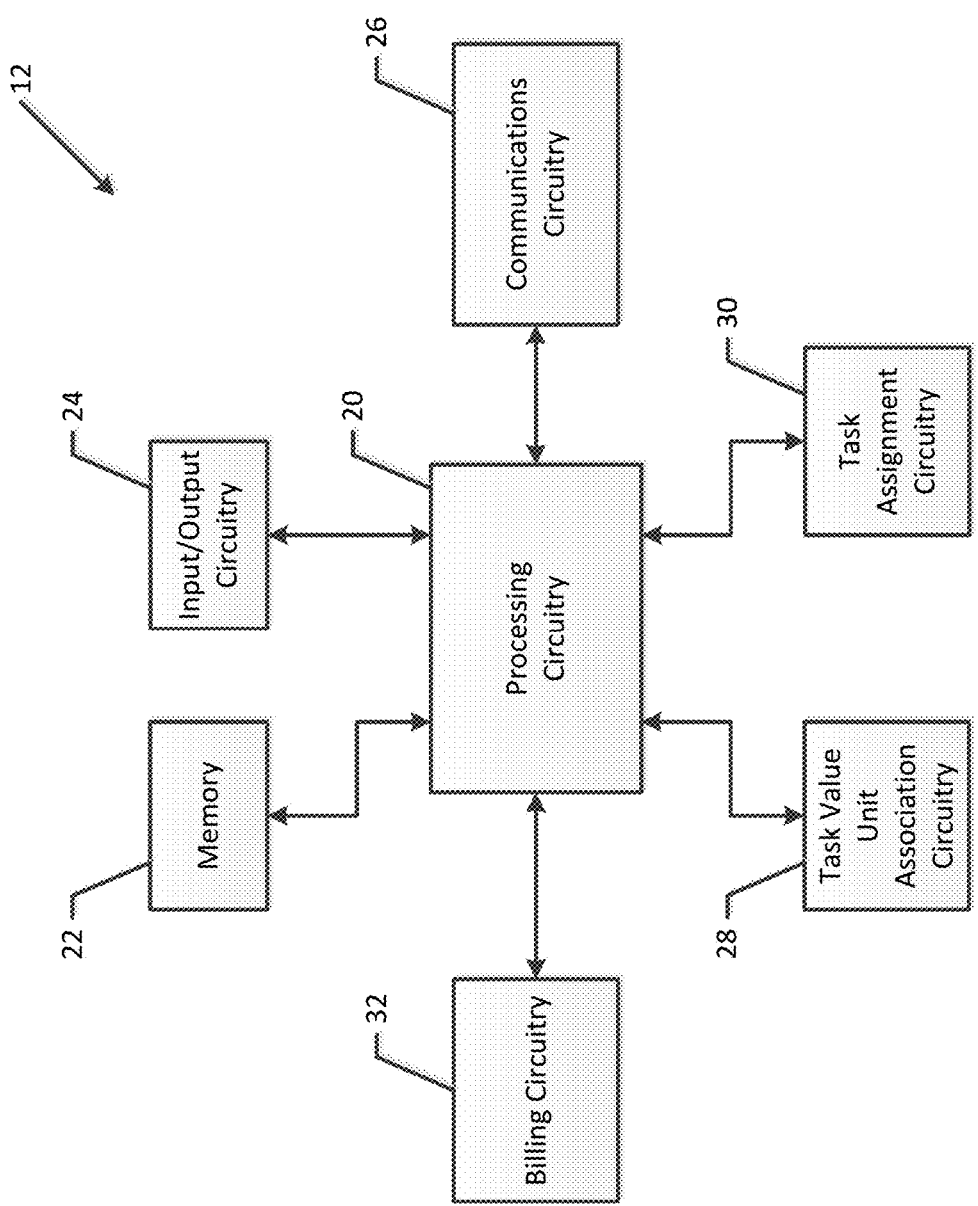
Figure 3:
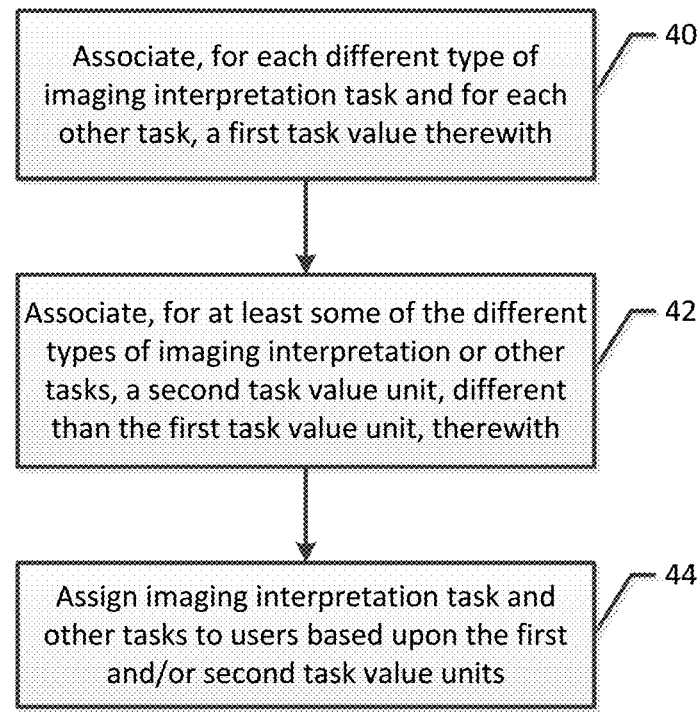
Figure 5:
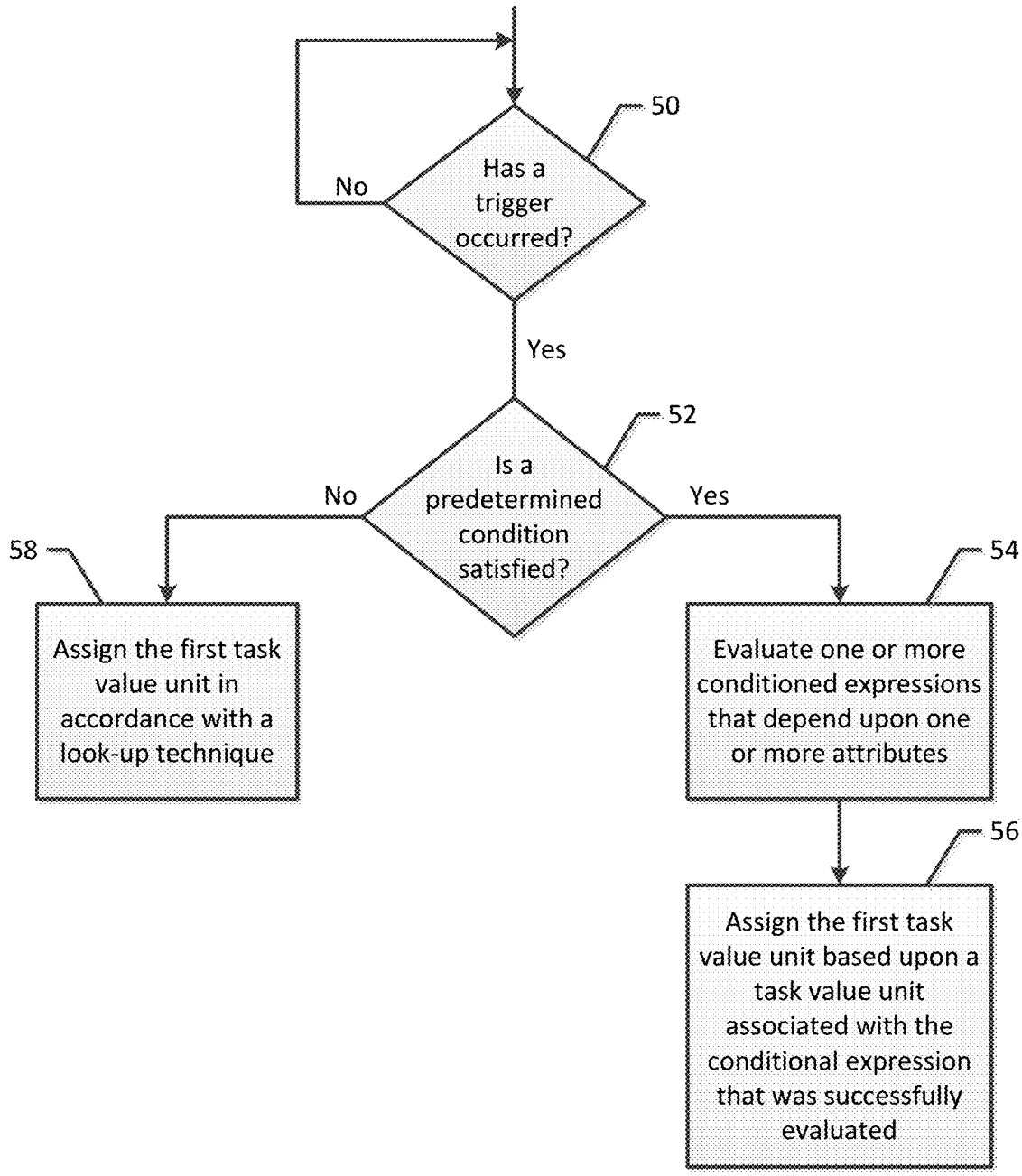

Having thus described certain embodiments of the invention in general terms, reference will now be made to the accompanying drawings, which are not necessarily drawn to scale, and wherein:

FIG. 1 is a block diagram of a system for utilizing task value units for imaging interpretation and other tasks in accordance with an example embodiment of the present invention;

FIG. 2 is a block diagram of an apparatus that may be specifically configured to utilize task value units for imaging interpretation and other tasks in accordance with an example embodiment of the present invention;

FIG. 3 is a flowchart illustrating operations performed, such as by the apparatus of FIG. 2, in accordance with an example embodiment of the present invention;

FIG. 4 is a table depicting a plurality of imaging interpretation and other tasks and associated task value units in accordance with an example embodiment of the present invention;

FIG. 5 is a flowchart illustrating operations performed, such as by the apparatus of FIG. 2, in order to determine the first task value unit in accordance with either a rule configuration and processing technique or a look-up technique in accordance with an example embodiment of the present invention;

FIG. 6a is a table illustrating three rotations defined to include a plurality of types of medical image studies in accordance with an example embodiment of the present invention; and FIG. 6b is a table illustrating the assignment of imaging interpretation tasks to a plurality of users associated with the respective rotations of FIG. 6a in accordance with an example embodiment of the present invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

A method, apparatus and computer program product are provided in accordance with an example embodiment in order to utilize task value units for imaging interpretations and other tasks. In this regard, the method, apparatus and computer program product of an example embodiment may utilize task value units in the assignment of imaging interpretation and other tasks to a plurality of users. By associating task value units not only with imaging interpretation tasks, but also with other tasks, the method, apparatus and computer program product of an example embodiment may assign the various tasks in a more fully informed manner by taking into account not only the other imaging interpretation tasks already assigned to a user, but also the other tasks that the user has been asked to perform. Further, a user is able to more completely document their work day, both in terms of the imaging interpretation tasks that they performed, as well as the other tasks performed by the user throughout the day.

FIG. 1 depicts an example embodiment of a system 10 that includes an apparatus 12 for utilizing task value units for imaging interpretation and other tasks. As shown in FIG. 1, the apparatus for utilizing task value units may be in communication with a plurality of users, each of which may be associated with or otherwise make use of a client device 14. In this regard, each client device may be embodied as a computing system for viewing image studies, such as a desktop computer, a laptop computer, a personal digital assistant, a tablet computer, a netbook computer, a picture archiving and communication system (PACS) workstation, an image reader, a PACS server 14a or the like that permits a user to review a medical image study and to provide a report or other feedback relating to the medical image study. The plurality of users, such as a plurality of radiologists, may be part of the same group of practitioners. However, in other embodiments, the plurality of users, such as the plurality of radiologists, may be members of different groups and may be affiliated with the same healthcare system, or even different healthcare systems.

The apparatus 12 utilizes task value units as described below for imaging interpretation and other tasks. With respect to imaging interpretation tasks, the imaging interpretation tasks may involve the review of various types of medical image studies. For the purposes of this application, the term "medical image study" refers to an image or set of images captured by a medical imaging device such as an x-ray, computed tomography (CT) scan, ultrasound (US) scan, magnetic resonance (MR) imaging scan, nuclear medicine (NM) hypatobiliary iminodiacetic acid (HIDA) scan or the like. The term should be understood to refer to both single, isolated images and sets of images. In some embodiments, the medical image study will include a set of metadata describing the file format of the image, the original capture resolution of the image, the type of device used to capture the image, the date the image was captured, a patient associated with the captured image, a viewing orientation of the image, a particular anatomical part of the patient represented in the image, one or more diagnostic codes, one or more procedure codes, or the like. In some embodiments, the medical image study may be stored in a Digital Imaging and Communications in Medicine (DICOM) file format. In some embodiments, the medical image study may be stored in other image formats such as JPEG, BMP, GIF, PNG or the like.

As to the other tasks, any other tasks that a user, such as a radiologist, is asked to perform during the course of their work day may be considered another task. For example, examples of other tasks that a radiologist may be asked to perform include peer reviews of a medical image study, technical question and answer tasks, critical result workflow tasks, teaching file management tasks, consultations, responding to inquiries from a referring practitioner, reviews of residents, performing rounds and other ad hoc tasks.

FIG. 2 illustrates a block diagram of an apparatus 12 in accordance with some example embodiments. The apparatus may be any computing device capable of associating task value units with respective tasks and then assigning the tasks based upon the task value units as described herein. For example, the apparatus may be implemented as any device capable of establishing a plurality client devices utilized by users, such as radiologists, to perform the respective tasks. The apparatus may be implemented as a standalone or rack-mounted server, a desktop computer, a laptop computer, a personal digital assistant, a tablet computer, a netbook computer, a PACS server, a PACS workstation or the like.

It should be noted that the components, devices or elements illustrated in and described with respect to FIG. 2 below may not be mandatory and thus some may be omitted in certain embodiments. Additionally, some embodiments may include further or different components, devices or elements beyond those illustrated in and described with respect to FIG. 2.

As illustrated in FIG. 2, an apparatus 12 may include processing circuitry 20, a memory 22, input/output circuitry 24, communications circuitry 26, task value unit association circuitry 28, task assignment circuitry 30 and billing circuitry 32. The apparatus may be configured to execute the operations described below with respect to FIGS. 3 and 5. Although these components 20-30 are described with respect to functional limitations, it should be understood that the particular implementations necessarily include the use of particular hardware. It should also be understood that certain of these components 20-30 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus should therefore be understood to include particular hardware configured to perform the functions associated with the particular circuitry as described herein.

The term "circuitry" should be understood broadly to include hardware and, in some embodiments, software for configuring the hardware. For example, in some embodiments, "circuitry" may include a processor, storage media, network interfaces, input/output devices, and the like. In some embodiments, other elements of the apparatus 12 may provide or supplement the functionality of particular circuitry. For example, the processing circuitry 20 may provide processing functionality, the memory 22 may provide storage functionality, the communications circuitry 26 may provide network interface functionality, and the like.

In some embodiments, the processing circuitry 20 (and/or co-processor or any other processing circuitry assisting or otherwise associated with the processor) may be in communication with the memory 22 via a bus for passing information among components of the apparatus 12. The memory may be non-transitory and may include, for example, one or more volatile and/or non-volatile memories. In other words, for example, the memory may be an electronic storage device (e.g., a computer readable storage medium). The memory may be configured to store information, data, content, applications, instructions, or the like, for enabling the apparatus to carry out various functions in accordance with example embodiments of the present invention.

The processing circuitry 20 may be embodied in a number of different ways and may, for example, include one or more processing devices configured to perform independently. Additionally or alternatively, the processing circuitry may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processing circuitry 20 may be configured to execute instructions stored in the memory 22 or otherwise accessible to the processing circuitry. Alternatively or additionally, the processing circuitry may be configured to execute hard-coded functionality. As such, whether configured by hardware or software methods, or by a combination thereof, the processing circuitry may represent an entity (e.g., physically embodied in circuitry) capable of performing operations according to an embodiment of the present invention while configured accordingly. Alternatively, as another example, when the processing circuitry is embodied as an executor of software instructions, the instructions may specifically configure the processing circuitry to perform the algorithms and/or operations described herein when the instructions are executed.

In some embodiments, the apparatus 12 may include input/output circuitry 24 that may, in turn, be in communication with processing circuitry 20 to provide output to the user and, in some embodiments, to receive an indication of a user input. The input/output circuitry may comprise a user interface and may include a display and may comprise a web user interface, a mobile application, a client device, a kiosk, or the like. In some embodiments, the input/output circuitry may also include a keyboard, a mouse, a joystick, a touch screen, touch areas, soft keys, a microphone, a speaker, or other input/output mechanisms. The processing circuitry and/or user interface circuitry comprising the processing circuitry may be configured to control one or more functions of one or more user interface elements through computer program instructions (e.g., software and/or firmware) stored on a memory accessible to the processing circuitry (e.g., memory 22, and/or the like).

The communications circuitry 26 may be any means such as a device or circuitry embodied in either hardware or a combination of hardware and software that is configured to receive and/or transmit data from/to a network and/or any other device, circuitry, or module in communication with the apparatus 12, such as to facilitate communication with the client devices 14. In this regard, the communications circuitry may include, for example, a network interface for enabling communications with a wired or wireless communication network. For example, the communications circuitry may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

The task value unit association circuitry 28 is configured to associate, for each of a plurality of different types of imaging interpretation tasks and for each of a plurality of other tasks, a first task value unit therewith. As described below, the task value unit association circuitry is also configured to associate, for at least some of the plurality of different types of imaging interpretation or other tasks, a second task value unit, different than the first task value unit, therewith The task assignment circuitry 30 is configured to assign imaging interpretation and other tasks to a plurality of users based at least partially upon at least one of the first and second task value units associated with the respective imaging interpretation and other tasks. As exemplified by the billing circuitry 32, the apparatus of an example embodiment also includes one or more additional modules configured to perform various functionality utilizing task value units representative of another type of weighting. With respect to the billing circuitry, the billing circuitry is configured to perform billing-related functionality utilizing task value units that are weighted for billing purposes as described below. The task value unit association circuitry, the task assignment circuitry, the billing circuitry and/or other modules may be embodied by the processing circuitry 20. Alternatively, the task value unit association circuitry, the task assignment circuitry, the billing circuitry and/or other modules may include a separate processor, specially configured field programmable gate array (FPGA), or application specific interface circuit (ASIC) to perform their respective functions. The task value unit association circuitry, the task assignment circuitry, the billing circuitry and/or other modules are therefore implemented using hardware components of the apparatus configured by either hardware or software for implementing these planned functions.

As described above and as will be appreciated based on this disclosure, embodiments of the present invention may comprise various means including entirely of hardware or any combination of software and hardware. Furthermore, embodiments may take the form of a computer program product on at least one non-transitory computer-readable storage medium, such as memory 22, having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Having now described an apparatus 12 configured to implement and/or support implementation of various example embodiments, features of several example embodiments will now be described. It will be appreciated that the following features are non-limiting examples of features provided by some example embodiments. Further, it will be appreciated that embodiments are contemplated within the scope of disclosure that implement various subsets or combinations of the features further described herein. Accordingly, it will be appreciated that some example embodiments may omit one or more of the following features and/or implement variations of one or more of the following features.

Referring now to FIG. 3, the operations performed, such as by the apparatus 12 of FIG. 2, in accordance with an example embodiment to the present invention are depicted. As shown at block 40, the task value unit association circuitry 28 is configured to associate a first task value unit with each of a plurality of different types of imaging interpretation tasks and for each of a plurality of other tasks. The first task value unit assigns a value or weight to a respective task based upon a predefined criteria. As described below, various predefined criteria may be employed depending upon the purpose to be served by the first task value units, such as depending upon whether the first task value units are to be utilized for workload management in which case the predefined criteria relates to the anticipated time to be expended to perform the task or for billing purposes in which case the predefined criteria relates to the anticipated revenue attributable to the performance of the task. With respect to imaging interpretation tasks and in an instance in which the first task value unit is to be utilized for workload management, the task value unit association circuitry of an example embodiment assigns the first task value unit based upon the relative complexity of the medical image study and correspondingly the length of time that the user is anticipated to expend performing the imaging interpretation task. Thus, a greater first task value unit is assigned to a more complex medical image study, while a smaller first task value unit is assigned to a more straightforward medical image study. By weighting the different imaging interpretation tasks depending upon the relative complexity of the medical image studies, a user, such as a radiologist, receives credit commensurate with the time that the user is anticipated to expend in the performance of the imaging interpretation task. By way of another example, in an instance in which the first task value unit is to be utilized for billing purposes, the task value unit association circuitry of an example embodiment assigns the first task value unit based upon the anticipated revenue to be generated from performance of the task with those tasks that are expected to be billed being assigned a greater first task value unit than those tasks that are not anticipated to be billed. The billing circuitry 32 of FIG. 2 may then be configured to utilize the first task value units for billing purposes.

By also associating a first task value unit with other tasks, other than the imaging interpretation tasks, that the user, such as a radiologist, is asked to perform, these other tasks may also be taken into account when assigning tasks to the users and the users may also receive credit for their performance of these other tasks in a comparable manner to the imaging interpretation tasks. The task value unit association circuitry 28 of an example embodiment is configured to assign a first task value unit based on the same predefined criteria that is utilized for the imaging interpretation tasks, such as the anticipated time to be expended to perform the task or the anticipated revenue attributable to the performance of the task, to each of the other tasks. For example, in an instance in which the first task value units are assigned for purposes of workload management, another tasks that is anticipated to consume a significant amount of time may be associated with a greater first task value unit than another task that is not anticipated to consume much time and which is correspondingly associated with a smaller first task value unit.

As shown in block 42, the task value unit association circuitry 28 is also configured to associate a second task value unit, different than the first task value unit, with at least some of the plurality of different types of imaging interpretation or other tasks. In this regard, the task value unit association circuitry need not associate a second task value unit with each task, but at least some of the tasks. The second task value unit serves a different purpose than the first task value unit, thereby resulting in the second task value unit being different than the first task value unit. For example, the first task value unit may be associated with a task for purposes of workload management and may thereby be assigned based on the time that a respective task is anticipated to require for its completion. In contrast, the second task value unit may be associated with the same task for purposes of billing ad may thereby be assigned based on the anticipated revenue, if any that is anticipated to be derived from performance of the task. By associating different types of task value units with the same tasks, such as the imaging interpretation tasks and the other tasks, different purposes may be served by the different task value units, such as for workload management, billing purposes or the like. As another example, different groups within the same healthcare system may wish to differently weight various tasks. Thus, the first and second task value units may represent the task value units assigned to the same tasks by different groups.

By way of example, FIG. 4 depicts a table in which a plurality of different types of tasks, such as imaging interpretation tasks, quality tasks, communication tasks and other tasks are identified. For each type of task, a plurality of different tasks of the same type are identified. For example, the quality task type include peer review tasks, critical result workflow tasks, teaching file management tasks, resident review tasks and technical question and answer tasks. For each task, a first task value unit is assigned. The first task value unit may be assigned for purposes of workload management such that the first task value unit is associated with a respective task based upon the time that performance of the task is anticipated to consume. In the example of FIG. 4, reading an MR Head w/wo (with/without) contrast image study is anticipated to take more time than reading an xray of a hand as indicated by the respective first task value units. In this example, responding to an inquiry by a referring clinician is anticipated to take approximately the same time as reading an MR Head w/wo contrast image study as indicated by the assignment of the same first task value unit. In the example of FIG. 4, the second task value unit is assigned for billing purposes such that only those tasks that are anticipated to be billed are assigned a second task value unit for use by the billing circuitry 32.

In an example embodiment, a baseline task value unit may be associated with a respective type of imaging procedure, such as a chest x-ray (CXR). However, the complexity of a medical imaging study that includes images captured by a respective type of imaging procedure may vary depending upon the purpose for which the medical imaging study is being reviewed. For example, a CXR that is reviewed as part of a cancer follow up may be reviewed much more quickly than a CXR that is reviewed to identify multiple stab wounds. Thus, different task value units may be assigned to the same type of procedure depending upon the purpose of the medical imaging study. In an example embodiment, the task value unit association circuitry 28 defines the task value units for the imaging interpretation tasks related to a respective type of procedure by starting with the baseline task value unit associated with the respective type of imaging procedure and then adding a modifier based upon the purpose of the medical imaging study and the corresponding anticipated complexity of the medical imaging study.

The first task value unit and the second task value unit are examples of task value unit types that may be pre-built into the apparatus 12. Additional types of task value units can be introduced into the apparatus through configuration, such as by the administrator of a healthcare system or the like. In this regard, a newly introduced type of task value unit would be given a name and would be of a numeric type. Once a type of task value unit is defined, the task value unit may be used in other parts of the apparatus, such as by the task value unit association circuitry 28, the task assignment circuitry 30 or the like to facilitate and/or receive functionality associated with task value units.

The task value unit association circuitry 28 of an example embodiment is configured to associate a first or second task value unit with a respective task based upon one or more attributes in accordance with a rule configuration and processing technique or in accordance with a look-up technique. In regards to a rule configuration and processing technique, the task value unit association circuitry is configured to initially determine that a trigger has occurred. In this regard, a trigger is an indication that a task value unit should be determined. Various triggers may be utilized including the receipt of an imaging interpretation task or other task for assignment. In response to occurrence of the trigger, the task value unit association circuitry is also configured to evaluate one or more conditional expressions that depend upon one or more attributes. By way of example, the one or more conditional expressions may join one or more conditions involving one or more respective attributes with boolean logic operations. In one example, a conditional expression considers attributes relating to the type of procedure and the facility in which the procedure was conducted. However, the conditional expressions may be reliant upon additional or different attributes in other embodiments including, for example, time of day (e.g., greater task value unit for overnight work than for midday work), holidays (e.g., greater task value unit for work performed on a holiday than on another day), experience level of the user (e.g., less task value unit for task performed by a more experienced radiologist), group to perform the task, patient (e.g., greater task value unit for a high-profile patient), etc.

Each conditional expression may be associated with a task value unit. The task value unit association circuitry 28 of this example embodiment is also configured to assign the task value unit based upon a task value unit associated with the conditional expression that was successfully evaluated. Although a plurality of conditional expressions may be evaluated, the task value unit association circuitry is configured to determine the one conditional expression that is successfully evaluated. The task value unit association circuitry of an example embodiment may be configured to address instances in which no conditional expression is successfully evaluated or in which two or more conditional expressions are successfully evaluated. In an instance in which no conditional expression is successfully evaluated, the task value unit association circuitry may be configured not to assign a task value unit or to assign a default task value unit, e.g., 1. In an instance in which two or more conditional expressions are successfully evaluated to produce two or more candidate task value units, the task value unit association circuitry may be configured to set the task value unit to be the minimum of the candidate task value units, the maximum of the candidate task value units or the average of the candidate task value units, or to maintain the task value unit as the last task value unit assigned or the first task value unit assigned.

In an instance in which one of the conditional expressions is successfully evaluated, the task value unit association circuitry assigns the task value unit to the respective task based on the task value unit that is associated with the successfully evaluated conditional expression, such as by setting the task value unit for the respective task equal to the task value unit that is associated with the successfully evaluated conditional expression. For example, in an instance in which the conditional expression is based on attributes relating to a particular procedure and a particular facility at which the procedure is conducted, a task that includes the particular procedure being performed at the particular facility will satisfy the respective condition such that the task value unit associated with the task is set equal to the task value unit associated with the successfully evaluated condition.

By way of example, a rules table may be predefined that defines a plurality of rules, each of which includes a trigger, a conditional expression and a resulting action relating to the assignment of a task value unit to a respective task. The rules table may be stored in memory 22 and may be referenced by the task value unit association circuitry 28 in order to assign a task value unit based upon the rules maintained within the rules table. One example of a rules table including three rules designated 1, 2 and 3 is as follows:

|     |                                              |
| --- | -------------------------------------------- |
| (1) | Trigger: task_added                          |
|     | Condition: (procedure_code = MR head)        |
|     | Action: Assign TVU = 4,                      |
| (2) | Trigger: task_added                          |
|     | Condition: (procedure_code = CT brain)       |
|     | Action: Assign TVU = 7 and                   |
| (3) | Trigger: task_added                          |
|     | Condition: (procedure_code = US leg)         |
|     | Action: Assign TVU = 9.                      |

In an instance in which a task is created for a CT brain study, such as may be received by the input/output circuitry 24 or the communication circuitry 26, the task value unit association circuitry 28 of this example embodiment executes each rule in the rules table that has a task_added trigger. In response, the task value unit association circuitry of this example embodiment will determine: that the conditional expression for (procedure_code=MR head) is false such that no action occurs, that the conditional expression for (procedure_code=CT brain) is true such that a task value unit (TVU) of 9 is assigned to the task and that the conditional expression for (procedure_code=US leg) is false such that no action occurs. Thus, the task value unit association circuitry will associate a task value unit of 9 with the CT brain study that was added.

As an alternative, the task value unit association circuitry 28 may utilize a look-up technique to determine the first and/or second task value units. In the look-up technique, a table may be defined, such as in memory 22, that stores every combination of attributes that are considered in the assignment of a task value unit to a respective task and that also stores the task value unit to be assigned to the respective task in an instance in which the particular combination of attributes is satisfied. In this example embodiment, in response to satisfaction of a trigger condition as described above, the task value unit association circuitry reviews the table to identify the listing having attributes that match the attributes associated with the respective task. The task value unit association circuitry then assigns the task value unit as is included within the respective listing to the respective task.

The tables utilized by the look-up technique in order to assign a task value unit to a task may utilize key value mapping based upon respective values for one or more attributes. In this regard, key value mapping defines one or more attributes that are considered keys in order to identify the listing of interest within the table for which the particular combination of attributes is satisfied by the task to be assigned. As such, the task value unit association circuitry 28 of this example embodiment is configured to determine the attributes that serve as the key values and to then identify the listing(s) within the table that have or are associated with the same key value attributes. The task value unit association circuitry is configured to then consider this subset of the listings within the table in order to identify the listing that satisfies all of the attributes associated with the task to be assigned and, in turn, to identify the task value unit for the respective listing.

The two techniques, that is, the rule configuration and processing technique and the look-up technique, each offer certain advantages. For example, the rule configuration and processing technique is relatively flexible with the conditional expressions being able to be modified and additional conditional expressions being capable of being added in order to accommodate the consideration of additional or different attributes. While the look-up technique may be less flexible with respect to the consideration of new or additional attributes since the table would need to be reconfigured to accommodate such new or additional attributes, the look-up technique may offer performance advantages in instances in which the number of different task value units that are to be assigned to respective tasks becomes large since the rule configuration and processing technique may require, in this circumstance, the time-consuming consideration of a correspondingly large number of conditional expressions. Additionally, the look-up technique may offer performance improvements in an instance in which the look-up table is implemented in a data structure such as a database with the table columns being database table fields which could be indexed for maximized single look-up performance.

As such, the task value unit association circuitry 28 of an example embodiment is configured to employ a hybrid approach in which the rule configuration and processing technique is utilized in some circumstances and the look-up technique is utilized in other circumstances. As such, the task value unit association circuitry is configured such that the rule processing and configuration technique is utilized in instances in which the rule configuration and processing technique offers performance advantages relative to the look-up technique, but the look-up technique is utilized in other instances in which the look-up technique offers performance advantages relative to the rule configuration and processing technique. As shown in FIG. 5, following the determination that a trigger has occurred as shown in block 50, the task value unit association circuitry of an example embodiment determines whether a predetermined condition is satisfied. See block 52. In an instance in which a predetermined condition is satisfied, one of the rule configuration and processing technique or the look-up technique is utilized in order to determine the task value unit. However, in an instance in which the predetermined condition is not satisfied, the other of the rule configuration and processing technique or the look-up technique is utilized to determine the task value unit.

In the illustrated embodiment, the task value unit association circuitry 28 is configured to perform the rule configuration and processing technique in an instance in which the predetermined condition is satisfied and to perform the look-up technique in an instance in which the predetermined condition is not satisfied. In this regard, in an instance in which the predetermined condition is satisfied, the task value unit association circuitry evaluates one or more conditional expressions that depend upon one or more attributes, as shown in block 54. As shown in block 56, the task value unit association circuitry then assigns the task value unit based upon a task value unit associated with the conditional expression that was successfully evaluated. However, in an instance in which the predetermined condition is not satisfied, the task value unit association circuitry assigns the task value unit in accordance with the look-up technique, as shown in block 58.

Although the task value unit association circuitry 28 may define the predetermined condition that determines which of the rule configuration and processing technique or the look-up technique is utilized, the predetermined condition of an example embodiment is dependent upon the value of an attribute. For example, in an instance in which the number of unique task value units is less than a predetermined amount, the task value unit association circuitry is configured to utilize the rule processing and configuration technique to determine the first task value unit, while in an instance in which the number of unique task value units equals or exceeds the predetermined amount, the task value unit association circuitry is configured to utilize the look-up technique in order to determine the first task value unit. As another example, the predetermined condition may be a predefined procedure, such as CT Brain or MR Head. As such, the task value unit association circuitry of this example embodiment is configured to provide for flexibility in the consideration of a wide variety of attributes and a correspondingly wide variety of conditional expressions in the assignment of task value units to a respective task, while doing so in an efficient manner even as the number of different task value units increases.

By way of a first example, the predetermined condition may be a CT Brain procedure. Thus, when the added task is for a CT Brain procedure, the look-up technique may be utilized with the rule configuration and processing technique being used for all other procedures. In a second example, the predetermined condition may be a MR Head procedure and a non-null location of the procedure. In an instance in which the added task is for a MR Head procedure and a value is provided for the location of the procedure, the look-up technique may be utilized with the task value unit set to 6 when the location is Ward 1, the task value unit is set to 8 when the location is Ward 2 and the task value unit is set to 5 when any other location is provided. For other procedures or for a MR Head procedure in which no value is provided for the location of the procedure, the rule configuration and processing technique may be utilized. As a third example, the predetermined condition may be a MR Head procedure and the absence of a location of the procedure. In an instance in which the added task is for a MR Head procedure and no value is provided for the location, the rule configuration and processing technique may be utilized. In this regard, in an instance in which the conditional expression of (Clinical_Indication="% Critical %") in which % is a wildcard, the task value unit is set to 15. In an instance in which the added task is for a different procedure or is for a MR Head procedure but a location of the procedure is provided, the look-up technique may be employed. As a fourth example, the predetermined condition may be may be a US Leg procedure and the number of unique task value units being less than a predefined threshold. In an instance in which the added task is for a US Leg procedure and the number of unique task value units is less than the predefined threshold, the rule configuration and processing technique may be employed, while the look-up technique may be otherwise utilized, such as for other procedures or in instances in which the number of unique task value units equals or exceeds the predefined threshold.

Referring now to block 44 of FIG. 3, the apparatus 12 also includes task assignment circuitry 30 configured to assign imaging interpretation and other tasks to a plurality of users based at least partially upon at least one of the first and second task value units associated with respective imaging interpretation and other tasks. For example, in an instance in which one of the task value units, such as the first task value unit, is associated with workload management, the task assignment circuitry of an example embodiment is configured to assign imaging interpretation and other tasks based upon the task value units associated with workload management, such as the first task value units of the example of FIG. 4. However, the task assignment circuitry may be configured to assign imaging interpretation and other tasks based upon various criteria. For example, the task assignment circuitry may be configured to assign tasks to a plurality of users, such as a plurality of radiologists, such that each user is assigned tasks having corresponding task value units that, in the aggregate, are within a predefined range of one another. Thus, even though one user may have many more tasks than another user, the aggregate amount of the task value units of the tasks assigned to the different users is maintained at a relatively similar level, thereby leveling the workload. In addition, by taking into account not only the task value units associated with imaging interpretation tasks, but also the task value units associated with other tasks, the task assignment circuitry is configured to assign tasks in a manner that considers the entirety of the workload of a user and that permits the performance of the user to be evaluated based not only upon the imaging interpretation tasks that are performed but also based upon the other tasks that are performed as a result of the consistent use of task value units for all of the various types of tasks.

As noted above, the task assignment circuitry 30 may be configured to assign the tasks based upon various other criteria. For example, the task assignment circuitry may maintain a predefined maximum aggregated task value such that no additional tasks are assigned to a user to whom tasks having task value units that in the aggregate exceed, in combination with the task value unit of the task to be assigned, the predetermined maximum aggregated task value. Alternatively, the task assignment circuitry may maintain a record of the historical performance of the users in terms of the task value units of the various tasks completed by the users. Thus, the task assignment circuitry may be configured to assign tasks in a manner consistent with the historical performance of the different users. Thus, a user who has historically completed tasks having task value units that in the aggregate greatly exceed the task unit values, in the aggregate, of the tasks performed by another user may be assigned a greater number of tasks or may be assigned tasks having a larger aggregate task value unit than other users as a result of the past performance of the user. As another example, such as in an instance in which a task to be assigned is designated to be of high priority, e.g., STAT, the task assignment circuitry may assign the task to the user who has the smallest number of high priority tasks or who has the smallest number of tasks that remain to be performed in their work list.

Prior to assigning tasks, the task assignment circuitry 30 of an example embodiment identifies the users who are eligible to receive the task assignment. In this regard, the task assignment circuitry may be configured to consider a plurality of criteria, such as the type of study, the type of patient, the current time, the specialty and sub-specialty of the user, the schedule of the user, user preferences or the like, in order to determine the users who are available and qualified to receive the task assignment. The task assignment circuitry then assigns the task in the manner described above to one of the eligible users.

In an example embodiment, the task assignment circuitry 30 utilizes a rotation in order to reduce the reliance of the assignment of tasks upon individual users. In this example embodiment, the task assignment circuitry is configured to define a rotation that includes a plurality of types of medical image studies. As shown in FIG. 6a, for example, a mammography rotation includes diagnostic mammography images, screening mammography images and general radiology mammography images, while a musculoskeletal (MSK) rotation includes an emergency room (ER)/in-patient MSK images, out-patient MSK images and general radiology MSK images, while a neurology rotation includes stroke protocols, ER/in-patient neurology images, out-patient neurology images and general radiology neurology images.

In the absence of workload balancing, the task assignment circuitry 30 of this example embodiment is also configured to assign the imaging interpretation tasks to a plurality of users associated with a rotation. Thus, in the foregoing example, FIG. 6b depicts an example in which radiologists A, B, C, D, E and F are assigned to the different rotations with at least two radiologists assigned to each rotation. The task assignment circuitry of this example embodiment then assigns the various tasks to a rotation, as opposed to an individual user, with the users associated with the respective rotation, at least upon the day of the assignment of the task, then being responsible for completing the assigned task. As such, in an instance in which one of the users is unavailable for a period of time, the other user assigned to the same rotation may complete the assigned tasks, thereby reducing any delay associated with completion of the assigned task.

In an instance in which the task assignment circuitry 30 employs workload balancing in conjunction with the assignment of imaging interpretation and other tasks, the task assignment circuitry identifies the radiologists who are eligible to receive a task based upon the rotation. From among the radiologists who are eligible to receive the task, the task assignment circuitry then assigns the task in a manner to balance the workload between the eligible radiologists, such as by assigning the task to the eligible radiologist who has the least number of tasks or the lowest aggregated amount of task value units for the assigned tasks.

Considering the example of FIGS. 6a and 6b in an instance in which the task assignment circuitry 30 employs workload balancing, the task assignment circuitry 30 would assign a new screening mammography task from 10 AM on October 2 to either Dr. C or Dr. E. Following the identification of Dr. C and Dr. E as eligible radiologists based upon the rotation, the task assignment circuitry may assign the screening mammography task based upon workload balancing utilizing the task value unit for the screening mammography task to a single one of Dr. C or Dr. E.

It will be understood that each element of the flowcharts, and combinations of elements in the flowcharts, may be implemented by various means, such as hardware, firmware, processor, circuitry, and/or other devices associated with execution of software including one or more computer program instructions. For example, one or more of the procedures described above may be embodied by computer program instructions. In this regard, the computer program instructions which embody the procedures described above may be stored by a memory 22 of an apparatus employing an embodiment of the present invention and executed by processing circuitry 20 of the apparatus. As will be appreciated, any such computer program instructions may be loaded onto a computer or other programmable apparatus (e.g., hardware) to produce a machine, such that the resulting computer or other programmable apparatus implements the functions specified in the flowchart blocks. These computer program instructions may also be stored in a computer-readable memory that may direct a computer or other programmable apparatus to function in a particular manner, such that the instructions stored in the computer-readable memory produce an article of manufacture the execution of which implements the function specified in the flowchart blocks. The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowchart blocks.

Accordingly, blocks of the flowcharts support combinations of means for performing the specified functions and combinations of operations. It will also be understood that one or more blocks of the flowcharts, and combinations of blocks in the flowcharts, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed is:

1. An apparatus for utilizing task value units for imaging interpretation and other tasks, the apparatus comprising:
   task value unit association circuitry of a picture archiving and communication system (PACS) computer, the task value unit association circuitry implemented by hardware components and configured to:
   for each of a plurality of different types of imaging interpretation tasks and for each of a plurality of other tasks, associate a first task value unit therewith; and
   for at least some of the plurality of different types of imaging interpretation or other tasks, associate a second task value unit, different than the first task value unit, therewith,
   wherein the at least some of the plurality of different types of imaging interpretation or other tasks have both first and second task value units associated therewith with the first task value unit being utilized for workload management and having a value that is based upon a first predefined criteria that relates to an anticipated time to be expended to perform the imaging interpretation or other task and the second task value unit being utilized for billing purposes and having a value that is based upon a second predefined criteria that relates to an anticipated revenue attributable to performance of the imaging interpretation or other task, wherein the task value unit association circuitry is configured to associate the first task value unit with the imaging interpretation or other task by:
  determining the first task value unit in accordance with one of a rule configuration and processing technique or a look-up technique in an instance in which a predetermined condition is satisfied; and
  determining the first task value unit in accordance with a different one of the rule configuration and processing technique or the look-up technique in an instance in which the predetermined condition is not satisfied,
wherein the task value unit association circuitry is configured such that the rule configuration and processing technique and the look-up technique are utilized separately, with the task value unit association circuitry configured to determine the first task value unit by the rule configuration and processing technique without utilization of the look-up technique or alternatively by the look-up technique without utilization of the rule configuration and processing technique,
wherein the rule configuration and processing technique defines a plurality of rules with each rule including a trigger, a conditional expression and an action relating to the assignment of a task value unit to a respective task,
wherein the look-up technique defines a table storing each of a plurality of combinations of attributes associated with the respective task,
wherein the predetermined condition is based on a number of unique task value units defining how many task value units having different values are associated with the imaging interpretation or other tasks, and
wherein the task value unit association circuitry is configured to perform the rule configuration and processing technique by:
  in response to occurrence of a trigger, evaluating one or more conditional expressions that depend upon one or more attributes; and
  performing the action by assigning the first task value unit based upon the task value unit associated with the conditional expression that was successfully evaluated; and
task assignment circuitry of the PACS computer, the task assignment circuitry implemented by hardware components and configured to assign imaging interpretation and other tasks to a plurality of users based at least partially upon at least one of the first and second task value units associated with the respective imaging interpretation and other tasks.

2. An apparatus according to claim 1 wherein the other tasks comprise one or more of peer review tasks, technical question and answer tasks, critical result workflow tasks, teaching file management tasks, consult tasks or resident review tasks.

3. An apparatus according to claim 1 wherein the task assignment circuitry is configured to assign imaging interpretation and other tasks to a plurality of users by defining a rotation comprising a plurality of types of medical image studies and assigning imaging interpretation tasks to a plurality of users associated with the rotation.

4. An apparatus according to claim 1 wherein the predetermined condition is also dependent upon a procedure relating to the imaging interpretation or other task.

5. An apparatus according to claim 1 wherein the table defined by the look-up technique is comprised of a data structure with table columns serving as database table fields, which are indexed.

6. A method of utilizing task value units for imaging interpretation and other tasks, the method implemented by a picture archiving and communication system (PACS) computer and comprising:
for each of a plurality of different types of imaging interpretation tasks and for each of a plurality of other tasks, associating a first task value unit therewith;
for at least some of the plurality of different types of imaging interpretation or other tasks, associating a second task value unit, different than the first task value unit, therewith,
  wherein the at least some of the plurality of different types of imaging interpretation or other tasks have both first and second task value units associated therewith with the first task value unit being utilized for workload management and having a value that is based upon a first predefined criteria that relates to an anticipated time to be expended to perform the imaging interpretation or other task and the second task value unit being utilized for billing purposes and having a value that is based upon a second predefined criteria that relates to an anticipated revenue attributable to performance of the imaging interpretation or other task,
wherein associating the first task value unit with the imaging interpretation or other task comprises:
  determining the first task value unit in accordance with one of a rule configuration and processing technique or a look-up technique in an instance in which a predetermined condition is satisfied; and
  determining the first task value unit in accordance with a different one of the rule configuration and processing technique or the look-up technique in an instance in which the predetermined condition is not satisfied,
wherein the rule configuration and processing technique and the look-up technique are utilized separately, with the first task value unit being determined by the rule configuration and processing technique without utilization of the look-up technique or alternatively by the look-up technique without utilization of the rule configuration and processing technique,
wherein the rule configuration and processing technique defines a plurality of rules with each rule including a trigger, a conditional expression and an action relating to the assignment of a task value unit to a respective task,
wherein the look-up technique defines a table storing each of a plurality of combinations of attributes associated with the respective task,
wherein the predetermined condition is based on a number of unique task value units defining how many task value units having different values are associated with the imaging interpretation or other tasks, and
wherein performing the rule configuration and processing technique comprises:
  in response to occurrence of a trigger, evaluating one or more conditional expressions that depend upon one or more attributes; and
  performing the action by assigning the first task value unit based upon the task value unit associated with the conditional expression that was successfully evaluated; and assigning imaging interpretation and other tasks to a plurality of users based at least partially upon at least one of the first and second task value units associated with the respective imaging interpretation and other tasks.

7. A method according to claim 6 wherein the other tasks comprise one or more of peer review tasks, technical question and answer tasks, critical result workflow tasks, teaching file management tasks, consult tasks or resident review tasks.

8. A method according to claim 6 wherein assigning imaging interpretation and other tasks to a plurality of users comprises defining a rotation comprising a plurality of types of medical image studies and assigning imaging interpretation tasks to a plurality of users associated with the rotation.

9. A method according to claim 6 wherein associating a first task value unit with an imaging interpretation or other task comprises determining the first task value unit in accordance with a look-up technique that utilizes key value mapping based upon respective values of one or more attributes.

10. A method according to claim 6 further comprising receiving input configuring an additional type of task value unit to serve a different purpose than the first and second task value units.

11. A method according to claim 6 wherein the predetermined condition is also dependent upon a procedure relating to the imaging interpretation or other task.

12. A method according to claim 6 wherein the table defined by the look-up technique is comprised of a data structure with table columns serving as database table fields, which are indexed.

13. A computer program product for utilizing task value units for imaging interpretation and other tasks, the computer program product comprising a non-transitory computer readable storage medium having program code portions stored thereon, the program code portions configured, upon execution by a picture archiving and communication system (PACS) computer, to:

for each of a plurality of different types of imaging interpretation tasks and for each of a plurality of other tasks, associate a first task value unit therewith;

for at least some of the plurality of different types of imaging interpretation or other tasks, associate a second task value unit, different than the first task value unit, therewith, wherein the at least some of the plurality of different types of imaging interpretation or other tasks have both first and second task value units associated therewith with the first task value unit being utilized for workload management and having a value that is based upon a first predefined criteria that relates to an anticipated time to be expended to perform the imaging interpretation or other task and the second task value unit being utilized for billing purposes and having a value that is based upon a second predefined criteria that relates to an anticipated revenue attributable to performance of the imaging interpretation or other task, wherein the program code portions configured to associate the first task value unit with the imaging interpretation or other task comprise program code portions configured, upon execution, to:

determine the first task value unit in accordance with one of a rule configuration and processing technique or a look-up technique in an instance in which a predetermined condition is satisfied; and determine the first task value unit in accordance with a different one of the rule configuration and processing technique or the look-up technique in an instance in which the predetermined condition is not satisfied, wherein the rule configuration and processing technique and the look-up technique are utilized separately, with the first task value unit being determined by the rule configuration and processing technique without utilization of the look-up technique or alternatively by the look-up technique without utilization of the rule configuration and processing technique, wherein the rule configuration and processing technique defines a plurality of rules with each rule including a trigger, a conditional expression and an action relating to the assignment of a task value unit to a respective task, wherein the look-up technique defines a table storing each of a plurality of combinations of attributes associated with the respective task, wherein the predetermined condition is based on a number of unique task value units defining how many task value units having different values are associated with the imaging interpretation or other tasks, and wherein the program code portions configured to perform the rule configuration and processing technique comprise program code portions configured, upon execution, to:

in response to occurrence of a trigger, evaluate one or more conditional expressions that depend upon one or more attributes; and perform the action by assigning the first task value unit based upon the task value unit associated with the conditional expression that was successfully evaluated; and assign imaging interpretation and other tasks to a plurality of users based at least partially upon at least one of the first and second task value units associated with the respective imaging interpretation and other tasks.

14. A computer program product according to claim 13 wherein the other tasks comprise one or more of peer review tasks, technical question and answer tasks, critical result workflow tasks, teaching file management tasks, consult tasks or resident review tasks.

15. A computer program product according to claim 13 wherein the program code portions configured to assign imaging interpretation and other tasks to a plurality of users comprise program code portions configured to define a rotation comprising a plurality of types of medical image studies and assigning imaging interpretation tasks to a plurality of users associated with the rotation.

16. A computer program product according to claim 13 wherein the predetermined condition is also dependent upon a procedure relating to the imaging interpretation or other task.

17. A computer program product according to claim 13 wherein the table defined by the look-up technique is comprised of a data structure with table columns serving as database table fields, which are indexed.

* * * * *